United States Patent [19]

Minai et al.

[11] Patent Number: 4,542,235

[45] Date of Patent: Sep. 17, 1985

[54] METHOD FOR PRODUCING AN OPTICALLY ACTIVE 2,2-DIMETHYLCYCLOPROPANECARBOXYLIC ACID

[75] Inventors: Masayoshi Minai, Moriyama; Tadashi Katsura, Suita; Kazuhiko Hamada; Gohfu Suzukamo, both of Ibaraki, all of Japan

[73] Assignee: Sumitomo Chemical Company, Limited, Osaka, Japan

[21] Appl. No.: 482,259

[22] Filed: Apr. 5, 1983

[30] Foreign Application Priority Data

Apr. 12, 1982 [JP] Japan ................................. 57-61237
Jan. 10, 1983 [JP] Japan ................................. 58-2600
Jan. 17, 1983 [JP] Japan ................................. 58-6348
Feb. 9, 1983 [JP] Japan ................................. 58-20982

[51] Int. Cl.$^4$ ............................................ C07B 19/00
[52] U.S. Cl. ..................................... 562/401; 562/506
[58] Field of Search ................................ 562/401, 506

[56] References Cited

U.S. PATENT DOCUMENTS 4,236,026 11/1980 Naumann ........................... 562/401
4,257,976 3/1981 Pavan et al. ....................... 562/401
4,337,352 6/1982 Naumann ........................... 562/401

Primary Examiner—Natalie Trousof
Assistant Examiner—Vera C. Clarke
Attorney, Agent, or Firm—Stevens, Davis, Miller & Mosher

[57] ABSTRACT

A method for producing an optically active 2,2-dimethylcyclopropanecarboxylic acid useful as an intermediate for dehydropeptidase I inhibitors, medicines and agricultural chemicals, which comprises reacting an optically active diphenylethylamine represented by the formula,

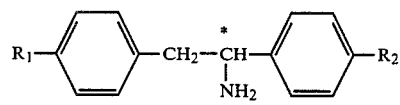

wherein $R_1$ and $R_2$ are each a hydrogen atom or a lower alkyl group, with 2,2-dimethylcyclopropanecarboxylic acid in a solvent to achieve the optical purification of said acid.

7 Claims, No Drawings

METHOD FOR PRODUCING AN OPTICALLY ACTIVE 2,2-DIMETHYLCYCLOPROPANECARBOXYLIC ACID

The present invention relates to a method for obtaining an optically active 2,2-dimethylcyclopropanecarboxylic acid which is useful as an intermediate for dehydropeptidase I inhibitors, medicines and agricultural chemicals, and a resolving reagent or a reagent for measuring the optical purity of optically active amines.

The conventionally well-known method for producing an optically active 2,2-dimethylcyclopropanecarboxylic acid is the optical resolution of dl-2,2-dimethylcyclopropanecarboxylic acid, and the well-known resolution method is (1) resolution with quinine [Japanese Patent Application Kokai (Laid-open) No. 51023/1980] or (2) resolution with d- or l-$\alpha$-phenethylamine (Specification of B.P. No. 1,260,847).

The method (1), however, has a problem in that quinine, very expensive as well as not available stably, should be used as the resolving reagent, and besides that the yield is low. The method (2) also has a problem in that there is obtained an optically active 2,2-dimethylcyclopropanecarboxylic acid alone of such a low optical purity that the optical rotation of its d-form is $+65°$ and that of its l-form is $-72°$. Neither of these methods, therefore, may be said to be a one for obtaining an optically active 2,2-dimethylcyclopropanecarboxylic acid of high optical purity advantageously in industry. Further, considering that said carboxylic acid is required to have an extremely high optical purity for use as an intermediate for medicines and agricultural chemicals and a reagent for measuring optical purity, the conventional methods are not satisfactory.

In view of that described above, the present inventors extensively studied to produce an optically active 2,2-dimethylcyclopropanecarboxylic acid of high optical purity in good yields and advantageously in industry, and as a result, attained the present invention.

The present invention provides a method for producing an optically active 2,2-dimethylcyclopropanecarboxylic acid which comprises reacting an optically active diphenylethylamine represented by the formula (I),

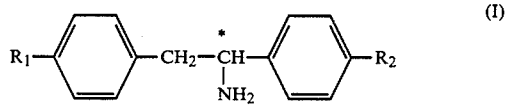

(I)

wherein $R_1$ and $R_2$ are each a hydrogen atom or a lower alkyl group, with 2,2-dimethylcyclopropanecarboxylic acid in a solvent to achieve the optical purification of said acid.

The present invention will be illustrated in detail hereinafter.

The 2,2-dimethylcyclopropanecarboxylic acid used as a starting material is its racemate or the acid containing the d- or l-form in excess. Such acid can easily be synthesized, for example, by the method described in J.O.C., 40, 456 (1975), Japanese Patent Publication No. 46835/1978 and the like.

As the optically active diphenylethylamine represented by the formula (I), as used as another starting material, there may be mentioned for example, d- or l-$\alpha$-phenyl-$\beta$-(p-tolyl)ethylamine, d- or l-$\alpha$-(p-tolyl)-$\beta$-phenylethylamine, d- or l-$\alpha$-phenyl-$\beta$-phenylethylamine and the like.

The optical purification treatment of 2,2-dimethylcyclopropanecarboxylic acid is carried out by reacting said carboxylic acid with an optically active diphenylethylamine represented by the foregoing formula (I) in a solvent to form a diastereomer salt, and slowly cooling the reaction mixture to deposit one of the optically active diastereomer salts which is then separated and decomposed.

The amount of the optically active diphenylethylamine used in formation of the diastereomer salt, is generally 0.3 to 1.2 times by mole, preferably 0.5 to 1.05 times by mole based on 2,2-dimethylcyclopropanecarboxylic acid.

As the solvent used in the above reaction, there may be mentioned for example alcohols such as methanol, ethanol, isopropanol, n-propanol, etc., ketones such as acetone, methyl ethyl ketone, etc., esters such as ethyl acetate, isopropyl acetate, etc., aromatic hydrocarbons such as toluene, benzene, etc., halogenated hydrocarbons such as chloroform, dichloromethane, etc., aliphatic hydrocarbons such as hexane, heptane, etc., ethers such as ethyl ether, tetrahydrofuran, etc., and mixtures thereof. Particularly, however, water-soluble solvents (e.g. methanol, ethanol, isopropanol, n-propanol, acetone), mixed solvents of the water-soluble ones with water and aromatic hydrocarbons are preferably used.

The amount of these solvents used is properly determined according to various conditions such as the kind and optical purity of 2,2-dimethylcyclopropanecarboxylic acid used as a starting material, the kinds of diphenylethylamines and solvents, and the like. Generally, however, the amount is in a range of 5 to 100 times by weight based on the 2,2-dimethylcyclopropanecarboxylic acid.

The reaction temperature may optionally be selected within a range of $-20°$ C. to the boiling point of the solvent used, but preferably, it is not less than a temperature at which the formed diastereomer salt is deposited.

After the optically active diastereomer salts have been formed by the foregoing reaction, the reaction mixture is slowly cooled to deposit one of the salts. The crystal obtained may be purified, if necessary, by repeating recrystallization.

The crystal thus obtained is then filtered off, dried if necessary and decomposed with an acid or alkali. When an acid is used for the decomposition, hydrochloric acid, sulfuric acid, phosphoric acid, acetic acid or the like is used, and the released optically active 2,2-dimethylcyclopropanecarboxylic acid is extraction-isolated with an organic solvent such as toluene, benzene, chloroform, ethyl acetate, ethyl ether, etc.

When an alkali is used for the decomposition, sodium hydroxide, potassium hydroxide or the like is used, and by extracting the decomposition solution with an organic solvent, the optically active diphenylethylamine used as a resolving reagent moves to the organic solvent layer, while said optically active carboxylic acid stays as a salt in the aqueous layer. On neutralizing this aqueous layer with addition of an acid and extracting with an organic solvent, the optically active 2,2-dimethylcyclopropanecarboxylic acid is extracted into the organic layer.

In this case, the same acid and organic solvent as described above are used for neutralization and extraction, respectively.

After formation of the diastereomer salts, from the filtrate after removing the crystal of one optically active diastereomer salt by filtration is obtained, the other diastereomer salt containing an excess of 2,2-dimethylcyclopropanecarboxylic acid having an opposite optical activity, by removing the solvent therefrom. Said acid can be isolated by recrystallizing said diastereomer salt and applying the same decomposition and after-treatment as above, or re-dissolving said diastereomer salt in the foregoing solvent, deposition-separating the salt by adding a seed crystal to the resulting solution and then applying the same decomposition and after-treatment as above to the crystal obtained.

In this way, d- or l-2,2-dimethylcyclopropanecarboxylic acid is obtained with good efficiency, and the optically active phenylethylamine used also can be recovered.

Such optical purification will be illustrated hereinafter with reference to specific compounds.

When said carboxylic acid is a racemic 2,2-dimethylcyclopropanecarboxylic acid and the optically active diphenylethylamine represented by the formula (I) is d-α-phenyl-β-(p-tolyl)ethylamine, a diastereomer salt obtained by deposition is that of l-2,2-dimethylcyclopropanecarboxylic acid with d-α-phenyl-β-(p-tolyl)ethylamine, the diastereomer salt of d-2,2-dimethylcyclopropanecarboxylic acid with d-α-phenyl-β-(p-tolyl)ethylamine being present in the filtrate. This means, therefore, the l-2,2-dimethylcyclopropanecarboxylic acid is obtained from the crystal part by applying the aforementioned operation, and while that d-2,2-dimethylcyclopropanecarboxylic acid is obtained by further purification of the filtrate part. When the foregoing d-form α-phenyl-β-(p-tolyl)ethylamine is therefore replaced by the l-form one, an opposite result to the foregoing one is obtained, that is, d-2,2-dimethylcyclopropanecarboxylic acid is obtained from the crystal part and l-2,2-dimethylcyclopropanecarboxylic acid is obtained by purifying the filtrate part.

But, when d-α-phenyl-β-(p-tolyl)ethylamine is replaced by d-α-phenyl- β-phenylethylamine, the diastereomer salt obtained from the crystal part is that of d-2,2-dimethylcyclopropanecarboxylic acid with d-α-phenyl-β-phenylethylamine, the diastereomer salt of l-2,2-dimethylcyclopropanecarboxylic acid with d-α-phenyl-β-phenylethylamine being present in the filtrate part. Consequently, d-2,2-dimethyloyclopropanecarboxylic acid is obtained from the crystal part by applying the foregoing operation and l-2,2-dimethylcyclopropanecarboxylic acid is obtained by purifying the filtrate part, this result being opposite to the foregoing one obtained with d-α-phenyl-β-(p-tolyl)ethylamine.

In the optical purification of the present invention, as described above, the optical rotatory power of an optically active 2,2-dimethylcyclopropanecarboxylic acid obtained from the crystal part is not always dependent upon the optical rotatory power of the optically active diphenylethylamine used, but varies with the kind of the diphenylethylamine.

Further, when 2,2-dimethylcyclopropanecarboxylic acid contains either one of its d-form or l-form in excess, particularly in an excess rate of not less than 15%, preferably not less than 30%, an optically active 2,2-dimethylcyclopropanecarboxylic acid alone contained in optical excess is obtained as a diastereomer salt independently of the kind and optical rotatory power of the optically active diphenylethylamine used.

For example, when the 2,2-dimethylcyclopropanecarboxylic acid is a d-rich one, the crystal deposited as a diastereomer salt is always the salt of d-2,2-dimethylcyclopropanecarboxylic acid independently of the kind and optical rotatory power of the optically active diphenylethylamine of the formula (I). As described above, when either one of the d-form or l-form is present in excess, its optical purification is achieved with very good efficiency, particularly independently of the kind and optical rotatory power of the optically active diphenylethylamine used. Such a case is not yet known.

Next, the present invention will be illustrated with reference to the following examples.

EXAMPLE 1

Thirty grams of 2,2-dimethylcyclopropanecarboxylic acid, 51.9 g of d-α-phenyl-β-phenylethylamine, 500 ml of isopropyl aclohol and 500 ml of water were fed to a flask, followed by refluxing for 30 minutes. Thereafter, 180 mg of the crystal of the diastereomer salt of d-2,2-dimethylcyclopropanecarboxylic acid with d-α-phenyl-β-phenylethylamine, as separately prepared, was added at 40° C. as seed crystal. The contents of the flask were then slowly cooled to 20° C., and the deposited crystal was filtered off.

The crystal obtained was recrystallized from a mixed solvent of 250 ml of isopropyl alcohol and 250 ml of water to obtain 28.9 g of a crystal.

To 28.9 g of this crystal were added 100 ml of ethyl ether and 25 ml of water, and to the resulting mixture was added 35.6 g of 10% aqueous hydrochloric acid to decompose the salt, whereby d-2,2-dimethylcyclopropanecarboxylic acid released was extracted into the organic layer. The organic layer was washed with water, and after removing the ether by evaporation, the residual liquor was further distilled to obtain 10.3 g of d-2,2-dimethylcyclopropanecarboxylic acid (yield, 34.3%).

| $[\alpha]_D^{20}$ + 147.1° (c = 1, chloroform) | |
|---|---|
| Enantiometric excess of the d-form | 99.5% |
| Content | 99.2% |

The excess rate was obtained by esterifying the acid with l-menthol and measuring the diastereomer obtained by gas chromatography.

EXAMPLE 2

Thirty grams of 2,2-dimethylcyclopropanecarboxylic acid, 55.5 g of d-α-phenyl-β-(p-tolyl)ethylamine, 240 ml of methanol and 60 ml of water were fed to a flask, followed by refluxing for 30 minutes. Thereafter, 180 mg of the crystal of the diastereomer salt of l-2,2-dimethylcyclopropanecarboxylic acid with d-α-phenyl-β-(p-tolyl)ethylamine, as separately prepared, was added at 35° to 40° C. as seed crystal. The contents of the flask were then slowly cooled to 20° C., and the deposited crystal was filtered off.

The crystal obtained was recrystallized from a mixed solvent of 250 ml of methanol and 250 ml of water to obtain 28.5 g of a crystal.

To 28.5 g of this crystal were added 100 ml of ethyl ether and 25 ml of water, and to the resulting mixture was added 33.6 g of 10% aqueous hydrochloric acid to decompose the salt, whereby l-2,2-dimethylcyclopropanecarboxylic acid released was extracted into the organic layer.

The organic layer was washed with water, and after removing the ether by evaporation, the residual liquor was further distilled to obtain 9.79 g of l-2,2-dimethylcyclopropanecarboxylic acid (yield, 32.6%).

| $[\alpha]_D^{20} - 146.7°$ (c = 1, chloroform) | |
|---|---|
| Enantiometric excess of the l-form | 99.4% |
| Content | 99.3% |

EXAMPLE 3

Thirty grams of 2,2-dimethylcyclopropanecarboxylic acid, 55.5 g of l-α-(p-tolyl)-β-phenylethylamine, 500 ml of isopropyl alcohol and 500 ml of water were fed to a flask, followed by refluxing for 30 minutes. Thereafter, 180 mg of the crystal of the diastereomer salt of d-2,2-dimethylcyclopropanecarboxylic acid with l-α-(p-tolyl)-β-phenylethylamine, as separately prepared, was added at 40° C. as seed crystal. The contents of the flask were then slowly cooled to 20° C., and the deposited crystal was filtered off.

The crystal obtained was recrystallized from a mixed solvent of 250 ml of isopropyl alcohol and 250 ml of water to obtain 28.2 g of a crystal.

To 28.2 g of this crystal were added 100 ml of ethyl ether and 25 ml of water, and to the resulting mixture was added 33.2 g of 10% aqueous hydrochloric acid to decompose the salt, whereby d-2,2-dimethylcyclopropanecarboxylic acid released was extracted into the organic layer.

The organic layer was washed with water, and after removing the ether by evaporation, the residual liquor was further distilled to obtain 9.70 g of d-2,2-dimethylcyclopropanecarboxylic acid (yield, 32.3%).

| $[\alpha]_D^{20} + 146.3°$ (c = 1, chloroform) | |
|---|---|
| Enantiometric excess of the d-form | 99.2% |
| Content | 99.1% |

EXAMPLE 4

Thirty grams of 2,2-dimethylcyclopropanecarboxylic acid, 55.5 g of l-α-phenyl-β-(p-tolyl)ethylamine, 240 ml of methanol and 60 ml of water were fed to a flask, followed by refluxing for 30 minutes. Thereafter, 180 mg of the crystal of the diastereomer salt of d-2,2-dimethylcyclopropanecarboxylic acid with l-α-phenyl-β-(p-tolyl)ethylamine, as separately prepared, was added at 40° C. as seed crystal. The contents of the flask were then slowly cooled to 20° C., and the deposited crystal was filtered off.

The crystal obtained was recrystallized from a mixed solvent of 250 ml of methanol and 250 ml of water to obtain 28.6 g of a crystal.

To 28.6 g of this crystal were added 100 ml of ethyl ether and 25 ml of water, and to the resulting mixture was added 33.7 g of 10% aqueous hydrochloric acid to decompose the salt, whereby d-2,2-dimethylcyclopropanecarboxylic acid released was extracted into the organic layer. The organic layer was washed with water, and after removing the ether by evaporation, the residual liquor was further distilled to obtain 9.83 g of d-2,2-dimethylcyclopropanecarboxylic acid (yield, 32.8%).

| $[\alpha]_D^{20} + 146.4°$ (c = 1, chloroform) | |
|---|---|
| Enantiometric excess of the d-form | 99.3% |
| Content | 99.3% |

EXAMPLE 5

Thirty grams of 2,2-dimethylcyclopropanecarboxylic acid, 51.9 g of l-α-phenyl-β-phenylethylamine and 2 liters of benzene were fed to a flask, followed by refluxing for 30 minutes. Thereafter, 180 mg of the crystal of the diastereomer salt of l-2,2-dimethylcyclopropanecarboxylic acid with l-α-phenyl-β-phenylethylamine, as separately prepared, was added at 50° to 45° C. as seed crystal. The contents of the flask were then slowly cooled to 20° C., and the deposited crystal was filtered off. The crystal obtained was recrystallized from a mixed solvent of 250 ml of isopropyl alcohol and 250 ml of water to obtain 28.6 g of a crystal.

To 28.6 g of this crystal were added 100 ml of ethyl ether and 25 ml of water, and to the resulting mixture was added 35.2 g of 10% aqueous hydrochloric acid to decompose the salt, whereby l-2,2-dimethylcyclopropanecarboxylic acid released was extracted into the organic layer. The organic layer was washed with water, and after removing the ether by evaporation, the residual liquor was further distilled to obtain 10.2 g of l-2,2-dimethylcyclopropanecarboxylic acid (yield, 34.0%).

| $[\alpha]_D^{20} - 147.2°$ (c = 1, chloroform) | |
|---|---|
| Enantiometric excess of the l-form | 99.4% |
| Content | 99.3% |

EXAMPLE 6

From the filtrate after removing the deposited crystal by filtration in Example 2, was removed the solvent by evaporation by concentration under reduced pressure.

The solid obtained, 250 ml of methanol and 250 ml of water were fed to a flask, followed by refluxing for 30 minutes. Thereafter, 180 mg of the crystal of the diastereomer salt of d-2,2-dimethylcyclopropanecarboxylic acid with d-α-phenyl-β-(p-tolyl)ethylamine, as separately prepared, was added at 45° to 50° C. as seed crystal. The contents of the flask were then slowly cooled to 20° C., and the deposited crystal was filtered off.

To 27.9 g of the crystal obtained were added 100 ml of ethyl ether and 25 ml of water, and to the resulting mixture was added 32.9 g of 10% aqueous hydrochloric acid to decompose the salt, whereby d-2,2-dimethylcyclopropanecarboxylic acid released was extracted into the organic layer. The organic layer was washed with water, and after removing the ether by evaporation, the residual liquor was further distilled to obtain 9.59 g of d-2,2-dimethylcyclopropanecarboxylic acid (yield, 32.0%).

| $[\alpha]_D^{20} + 146.5°$ (c = 1, chloroform) | |
|---|---|
| Enantiometric excess of the d-form | 99.2% |
| Content | 99.3% |

EXAMPLE 7

From the filtrate after removing the deposited crystal by filtration in Example 1, was removed the solvent by evaporation by concentration under reduced pressure.

The solid obtained, 250 ml of isopropyl alcohol and 250 ml of water were fed to a flask, followed by refluxing for 30 minutes. Thereafter, 180 mg of the crystal of the diastereomer salt of l-2,2-dimethylcyclopropanecarboxylic acid with d-α-phenyl-β-phenylethylamine, as separately prepared, was added at 45° to 50° C. as seed crystal. The contents of the flask were then slowly cooled to 20° C., and the deposited crystal was filtered off.

To 27.5 g of the crystal obtained were added 100 ml of ethyl ether and 25 ml of water, and to the resulting mixture was added 33.8 g of 10% aqueous hydrochloric acid to decompose the salt, whereby l-2,2-dimethylcyclopropanecarboxylic acid released was extracted into the organic layer. The organic layer was washed with water, and after removing the ether by evaporation, the residual liquor was further distilled to obtain 9.86 g of l-2,2-dimethylcyclopropanecarboxylic acid (yield, 32.9%).

| | |
|---|---|
| $[\alpha]_D^{20}$ − 146.8° (c = 1, chloroform) | |
| Enantiometric excess of the l-form | 99.3% |
| Content | 99.1% |

EXAMPLE 8

From the filtrate after removing the deposited crystal by filtration in Example 5, was removed the solvent by evaporation.

The solid obtained, 300 ml of isopropyl alcohol and 200 ml of water were fed to a flask, followed by refluxing for 30 minutes. Thereafter, the reaction solution was allowed to cool to 15° C., and the deposited crystal was filtered off. To 24.8 g of the crystal obtained were added 100 ml of ether and 25 ml of water, and to the resulting mixture was added 30.4 g of 10% aqueous hydrochloric acid to decompose the salt, whereby d-2,2-dimethylcyclopropanecarboxylic acid released was extracted into the organic layer. The organic layer was washed with water, and after removing the ether by evaporation, the residual liquor was further distilled to obtain 8.87 g of d-2,2-dimethylcyclopropanecarboxylic acid (yield, 29.6%).

| | |
|---|---|
| $[\alpha]_D^{20}$ 145.2° (c = 1, chloroform) | |
| Enantiometric excess of the d-form | 98.6% |
| Content | 99.0% |

EXAMPLE 9

Thirty grams of 2,2-dimethylcyclopropanecarboxylic acid (excess rate of the d-form, 58.4%), 55.5 g of d-α-phenyl-β-(p-tolyl)ethylamine and 2 liters of benzene were fed to a flask, followed by refluxing for 1 hour. Thereafter, 180 mg of the crystal of the diastereomer salt of d-2,2-dimethylcyclopropanecarboxylic acid with d-α-phenyl-β-(p-tolyl)-ethylamine, as separately prepared, was added at 30° to 40° C. as seed crystal. The contents of the flask were then slowly cooled to 10° C., and the deposited crystal was filtered off.

The crystal obtained was further recrystallized from 18 times its weight, expressed in part by weight, of benzene to obtain 44.1 g of a crystal.

Thereafter, to a mixed liquor comprising 43.0 g of the salt obtained here, 200 ml of ethyl ether and 50 ml of water was added 56 g of 10% aqueous hydrochloric acid to decompose the salt, whereby d-2,2-dimethylcyclopropanecarboxylic acid released was extracted into the organic layer. The organic layer was washed with water, and after removing the ether by evaporation, the residual liquor was distilled to obtain 14.6 g of d-2,2-dimethylcyclopropanecarboxylic acid (yield, 50% based on the fed carboxylic acid).

$[\alpha]_D^{20}$ 145.1° (c=1, chloroform)
Enantiometric excess of the d-form 98.4%

EXAMPLE 10

Fifteen grams of 2,2-dimethylcyclopropanecarboxylic acid (excess rate of the d-form, 73.9%), 240 ml of isopropyl alcohol, 320 ml of water and 27.8 g of d-α-phenyl-β-(p-tolyl)ethylamine were added to a flask, followed by refluxing for 30 minutes. Thereafter, 90 mg of the same seed crystal as used in Example 9 was added at 45° to 50° C., the contents of the flask were slowly cooled to 15° C. and the deposited crystal was filtered off. Thus, 30.5 g of a salt was obtained.

Thereafter, 25 g of the salt obtained here, 120 ml of ethyl ether and 30 ml of water were fed to a flask, and 32 g of 10% aqueous hydrochloric acid was added to decompose the salt. According to Example 9, the subsequent after-treatment, purification and distillation of the residue obtained were carried out.

Amount obtained, 8.63 g (yield, 70.2% based on the fed carboxylic acid)

| | |
|---|---|
| $[\alpha]_D^{20}$ 146.4° (c = 1, chloroform) | |
| Enantiometric excess of the d-form | 99.8% |
| Content | 98.9% |

EXAMPLE 11

11.4 Grams of 2,2-dimethylcyclopropanecarboxylic acid (excess rate of the d-form, 81.5%), 21.1 g of d-α-phenyl-β-(p-tolyl)ethylamine and 500 ml of toluene were fed to a flask, followed by refluxing for 1 hour. Thereafter, 60 mg of the same seed crystal as used in Example 10 was added at 55° to 60° C., the contents of the flask were slowly cooled to 20° C. and the deposited crystal was filtered off.

The crystal obtained was further recrystallized from 15 times its weight, expressed in part by weight, of toluene to obtain 20.5 g of a crystal.

Thereafter, the crystal obtained here, 50 ml of toluene and 30 ml of water were fed to a flask, and 27 g of 10% aqueous hydrochloric acid was added to the mixture to decompose the salt. According to Example 9, the subsequent after-treatment and purification were carried out.

Amount obtained, 7.81 g (yield, 68.5%)
Enantiometric excess of the d-form 98.3%

EXAMPLE 12

After reaction was carried out in the same manner as in Example 11 except that 500 ml of toluene was replaced by 200 ml of methanol plus 200 ml of water, and the resulting mixture was slowly cooled to 20° C. The amount of the deposited crystal was 19.7 g.

Thereafter, 19 g of the salt obtained here, 50 ml of toluene and 30 ml of water were fed to a flask, and 26 g of 10% aqueous hydrochloric acid was added to the mixture to decompose the salt. According to Example 10, the subsequent after-treatment and purification were carried out.

Amount obtained 6.63 g (60.3%)
Enantiometric excess of the d-form 97.8%

EXAMPLE 13

22.8 Grams of 2,2-dimethylcyclopropanecarboxylic acid (excess rate of the d-form, 75.1%), 38.0 g of d-α-phenyl-β-(p-tolyl)ethylamine, 400 ml of water and 400 ml of isopropyl alcohol were added to a flask, followed by refluxing for 30 minutes. Thereafter, 140 mg of the same seed crystal as used in Example 9 was added at 45° C., the contents of the flask were slowly cooled to 15° C., and the deposited crystal was filtered off. Thus, 44.9 g of a salt was obtained.

Thereafter, 32.5 g of the salt obtained here, 150 ml of toluene and 50 ml of water were fed to a flask, and 24 g of 20% sodium hydroxide was added to the mixture to decompose the salt. The aqueous layer was separated, 46.8 g of 10% hydrochloric acid was added thereto, and the released carboxylic acid was extracted with 80 ml of ethyl ether. According to Example 9, the subsequent after-treatment, purification and distillation of the residue obtained were carried out. From the toluene layer was recovered d-α-phenyl-β-(p-tolyl)ethylamine.

| Amount obtained 11.28 g (yield, 68.3% based on the fed carboxylic acid) | |
|---|---|
| $[\alpha]_D^{20}$ 146.1° (c = 1, chloroform) | |
| Enantiometric excess of the d-form | 99.7% |
| Content | 98.7% |

EXAMPLE 14

Thirty grams of 2,2-dimethylcyclopropanecarboxylic acid (excess rate of the d-form, 70%), 55.5 g of l-α-phenyl-β-(p-tolyl)ethylamine, 500 ml of isopropyl alcohol and 500 ml of water were fed to a flask, followed by refluxing for 30 minutes. Thereafter, 180 mg of the crystal of the diastereomer salt of d-2,2-dimethylcyclopropanecarboxylic acid with l-α-phenyl-β-(p-tolyl)ethylamine, as separately prepared, was added at 50° to 52° C. as seed crystal. The contents of the flask were then slowly cooled to 20° C., and the separated crystal was filtered off.

To 55.2 g of the crystal obtained were added 200 ml of ethyl ether and 50 ml of water, and to the resulting mixture was added 65 g of 10% aqueous hydrochloric acid to decompose the salt, whereby d-2,2-dimethylcyclopropanecarboxylic acid released was extracted into the organic layer.

The organic layer was washed with water, and after removing the ether by evaporation, the residual liquor was further distilled to obtain 19.6 g of d-2,2-dimethylcyclopropanecarboxylic acid (yield, 65.3%).

| $[\alpha]_D^{20}$ + 147.0° (c = 1, chloroform) | |
|---|---|
| Enantiometric excess of the d-form | 99.4% |
| Content | 99.3% |

EXAMPLE 15

Thirty grams of 2,2-dimethylcyclopropanecarboxylic acid (excess rate of the d-form, 50%), 55.5 g of l-α-phenyl-β-(p-tolyl)ethylamine and 2 liters of benzene were fed to a flask, followed by refluxing for 1 hour.

Thereafter, 180 mg of the same seed crystal as used in Example 14 was added, the contents of the flask were slowly cooled to 10° C., and the deposited crystal was filtered off.

The crystal obtained was recrystallized from 20 times its weight, expressed in part by weight, of benzene to obtain 39.2 g of a crystal.

To 39.2 g of this crystal were added 150 ml of ethyl ether and 40 ml of water, and to the resulting mixture was added 46 g of 10% aqueous hydrochloric acid to decompose the salt.

In the same manner as in Example 14, the subsequent after-treatment and purification were applied to obtain 13.7 g of d-2,2-dimethylcyclopropanecarboxylic acid (yield, 45.7%).

| $[\alpha]_D^{20}$ + 146.2° (c = 1, chloroform) | |
|---|---|
| Enantiometric excess of the d-form | 99.1% |
| Content | 99.4% |

EXAMPLE 16

Thirty grams of 2,2-dimethylcyclopropanecarboxylic acid (enantiometric excess of the d-form, 80%), 51.9 g of l-α-phenyl-β-phenylethylamine, 500 ml of methyl alcohol and 500 ml of water were fed to a flask, followed by refluxing for 30 minutes. Thereafter, 180 mg of the crystal of the diastereomer salt of d-2,2-dimethylcyclopropanecarboxylic acid with l-α-phenyl-β-phenylethylamine, as separately prepared, was added at 45° to 50° C. as seed crystal. The contents of the flask were then slowly cooled to 20° C., and the deposited crystal was filtered off.

To 54.1 g of the crystal obtained were added 200 ml of ethyl ether and 50 ml of water, and to the resulting mixture was added 66.5 g of 10% aqueous hydrochloric acid to decompose the salt. In the same manner as in Example 14, the subsequent after-treatment and purification were applied to obtain 19.3 g of d-2,2-dimethylcyclopropanecarboxylic acid (yield, 64.3%).

| $[\alpha]_D^{20}$ + 146.8° (c = 1, chloroform) | |
|---|---|
| Enantiometric excess of the d-form | 99.5% |
| Content | 99.2% |

EXAMPLE 17

Thirty grams of 2,2-dimethylcyclopropanecarboxylic acid (enantiometric excess of the l-form, 70%), 55.5 g of l-α-phenyl-β-(p-tolyl)ethylamine, 500 ml of isopropyl alcohol and 500 ml of water were fed to a flask, followed by refluxing for 30 minutes. Thereafter, 180 mg of the crystal of the diastereomer salt of l-2,2-dimethylcyclopropanecarboxylic acid with l-α-phenyl-β-(p-tolyl)ethylamine, as separately prepared, was added at 50° to 52° C. as seed crystal. The contents of the flask were then slowly cooled to 20° C., and the deposited crystal was filtered off.

To 54.3 g of the crystal obtained were added 200 ml of ethyl ether and 50 ml of water, and to the resulting mixture was added 64 g of 10% aqueous hydrochloric acid to decompose the salt, whereby l-2,2-dimethylcyclopropanecarboxylic acid released was extracted into the organic layer. The organic layer was washed with water, and after removing the ether by evaporation, the residual liquor was further distilled to obtain 18.5 g of l-2,2-dimethylcyclopropanecarboxylic acid (yield, 61.7%).

| $[\alpha]_D^{20}$ − 146.3° (c = 1, chloroform) | |
|---|---|
| Enantiometric excess of the l-form | 99.5% |
| Content | 98.7% |

EXAMPLE 18

Thirty grams of 2,2-dimethylcyclopropanecarboxylic acid (enantiometric excess of the l-form, 50%), 55.5 g of d-α-phenyl-β-(p-tolyl)ethylamine, 500 ml of methyl alcohol and 500 ml of water were fed to a flask, followed by refluxing for 30 minutes. Thereafter, 180 mg of the crystal of the salt of l-2,2-dimethylcyclopropanecarboxylic acid with d-α-phenyl-β-(p-tolyl)ethylamine, as separately prepared, was added at 48° to 50° C. as seed crystal. The contents of the flask were then slowly cooled to 20° C., and the deposited crystal was filtered off.

To 38.5 g of the crystal obtained were added 150 ml of ethyl ether and 40 ml of water, and to the resulting mixture was added 45.3 g of 10% aqueous hydrochloric acid to decompose the salt. According to Example 17, the subsequent after-treatment and purification were applied to obtain 13.2 g of l-2,2-dimethylcyclopropanecarboxylic acid (yield, 44%).

| $[\alpha]_D^{20}$ − 147.0° (c = 1, chloroform) | |
|---|---|
| Enantiometric excess of the l-form | 99.5% |
| Content | 99.2% |

EXAMPLE 19

Thirty grams of 2,2-dimethylcyclopropanecarboxylic acid (enantiometric excess of the l-form, 40%), 51.9 g of l-α-phenyl-β-phenylethylamine and 2 liters of benzene were fed to a flask, followed by refluxing for 1 hour. Thereafter, 180 mg of the crystal of the salt of l-2,2-dimethylcyclopropanecarboxylic acid with l-α-phenyl-β-phenylethylamine, as separately prepared, was added at 30° to 40° C. as seed crystal. The contents of the flask were then slowly cooled to 10° C., and the deposited crystal was filtered off.

The crystal obtained was recrystallized from 20 times its weight, expressed in part by weight, of benzene to obtain 33.2 g of a crystal.

To 33.2 g of the crystal obtained here were added 150 ml of ethyl ether and 40 ml of water, and to the resulting mixture was added 41 g of 10% aqueous hydrochloric acid to decompose the salt. According to Example 17, the subsequent after-treatment and purification were applied to obtain 11.9 g of l-2,2-dimethylcyclopropanecarboxylic acid (yield, 39.7%).

| $[\alpha]_D^{20}$ − 146.8° (c = 1, chloroform) | |
|---|---|
| Enantiometric excess of the l-form | 99.7% |
| Content | 99.0% |

EXAMPLE 20

Thirty grams of 2,2-dimethylcyclopropanecarboxylic acid (enantiometric excess of the l-form, 80%), 51.9 g of d-α-phenyl-β-phenylethylamine, 500 ml of methyl alcohol and 500 ml of water were fed to a flask, followed by refluxing for 30 minutes. Thereafter, 180 mg of the crystal of the salt of l-2,2-dimethylcyclopropanecarboxylic acid with d-α-phenyl-β-phenylethylamine, as separately prepared, was added at 45° to 50° C. as seed crystal. The contents of the flask were then slowly cooled to 20° C., and the deposited crystal was filtered off.

To 54.9 g of the crystal obtained were added 200 ml of ethyl ether and 50 ml of water, and to the resulting mixture was added 67.5 g of 10% aqueous hydrochloric acid to decompose the salt. According to Example 17, the subsequent after-treatment and purification were applied to obtain 20 g of l-2,2-dimethylcyclopropanecarboxylic acid (yield, 66.7%).

| $[\alpha]_D^{20}$ − 147.2° (c = 1, chloroform) | |
|---|---|
| Enantiometric excess of the l-form | 99.8% |
| Content | 99.3% |

EXAMPLE 21

From the filtrate after removing the obtained crystal by filtration in Example 11, was removed the solvent by evaporation by concentration under reduced pressure.

The solid obtained, 75 ml of methanol and 50 ml of water were fed to a flask, followed by refluxing for 30 minutes. Thereafter, 30 mg of the crystal of the diastereomer salt of d-2,2-dimethylcyclopropanecarboxylic acid with d-α-phenyl-β-(p-tolyl)ethylamine, as separately prepared, was added at 45° to 50° C. as seed crystal. The contents of the flask were then slowly cooled to 20° C., and the deposited crystal was filtered off.

To 6.30 g of the crystal obtained were added 40 ml of ethyl ether and 15 ml of water, and to the resulting mixture was added 7.5 g of 10% aqueous hydrochloric acid to decompose the salt, whereby d-2,2-dimethylcyclopropanecarboxylic acid released was extracted into the organic layer. According to Example 1, the subsequent after-treatment and purification were applied to obtain 2.14 g of d-2,2-dimethylcyclopropanecarboxylic acid (yield, 18.8% based on the fed 2,2-dimethylcyclopropanecarboxylic acid).

| $[\alpha]_D^{20}$ + 147.4° (c = 1, chloroform) | |
|---|---|
| Enantiometeric excess of the d-form | 99.5% |
| Content | 99.3% |

COMPARATIVE EXAMPLE 1

To a four-necked flask equipped with a stirrer and a thermometer were fed 17.1 g of 2,2-dimethylcyclopropanecarboxylic acid and 1.5 liters of benzene, and then a solution of 18.2 g of d(+)-α-methylbenzylamine in 750 ml of benzene was added thereto at room temperature.

After 20 hours, the crystal was collected by filtration and recrystallized four times from benzene to obtain 5.3 g of a crystal. Thereafter, this crystal was decomposed with 70 ml of N-aqueous hydrochloric acid, followed by extraction with 150 ml of ether. The ether layer was washed with water and dried over magnesium sulfate. After removing magnesium sulfate by filtration, the ether layer obtained was concentrated to obtain 1.82 g of (−)-2,2-dimethylcyclopropanecarboxylic acid (yield, 10.6%).

Optical rotation $[\alpha]_D^{20}$ −70.8° (c=1, chloroform)
Optical purity 47.7%

COMPARATIVE EXAMPLE 2

Reaction was carried out using the same raw materials, amounts used and operation as used in Comparative example 1 except that d(+)-α-methylbenzylamine was replaced by l(−)-α-methtlbenzylamine. Thus, 5.9 g of a crystal was obtained.

This crystal was decomposed with 80 ml of N-aqueous hydrochloric acid, followed by extraction with 150 ml of ether. In the same manner as in Comparative example 1, the subsequent after-treatment and purification were applied to obtain 1.91 g of (+)-2,2-dimethylcyclopropanecarboxylic acid (yield, 11.2%).

Optical rotation $[\alpha]_D^{26}$ +66.0° (c=1.0, chloroform)
Optical purity 44.9%

COMPARATIVE EXAMPLE 3

To the same apparatus as used in Comparative example 1 were added 23.1 g of 2,2-dimethylcyclopropanecarboxylic acid and 33 ml of water, and the pH of the resulting mixture was adjusted to 8.0 with about 10 ml of 50% aqueous sodium hydroxide solution. Thereafter, a solution of 38.4 g of quinine in a mixture of 60 ml of methanol and 30 ml of water, the pH of the water being previously adjusted to 7.1 by adding about 8 ml of conc. hydrochloric acid (this solution is in fact a quinine hydrochloride solution), was added to the foregoing reaction mixture which was then turned into solution by heating. On cooling the solution to 20° C., a crystal deposited. This solution was allowed to stand for two days at room temperature. Thereafter, the crystal was collected by filtration, washed with two 10-ml portions of water and then with two 10-ml portions of 50% aqueous ethanol to obtain 41.3 g of a crude crystal. This crude crystal was recrystallized from acetone to obtain 24.3 g of a crystal. This quinine salt was decomposed with 80 ml of 2% aqueous alkali solution and 100 ml of chloroform, and the resulting aqueous layer was acidified with 20% aqueous hydrochloric acid and then extracted with 100 ml of ether. The organic layer was washed with water, dried over magnesium sulfate and concentrated to obtain 4.1 g of (+)-2,2-dimethylcyclopropanecarboxylic acid (yield, 17.7%).

Optical rotation +143.0° (c=1, chloroform)
Optical purity 97.2%

What is claimed is:

1. A method for producing an optically active 2,2-dimethylcyclopropanecarboxylic acid which comprises reacting an optically active diphenylethylamine represented by the formula (I),

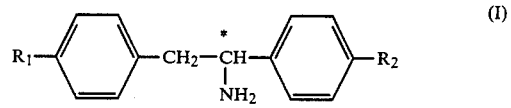

wherein $R_1$ and $R_2$ are each a hydrogen atom or a lower alkyl group, with 2,2-dimethylcyclopropanecarboxylic acid in a solvent to achieve the optical purification of said acid.

2. A method as described in claim 1, wherein said 2,2-dimethylcyclopropanecarboxylic acid is a one containing the d-form in excess, and said optically active 2,2-dimethylcyclopropanecarboxylic acid is d-2,2-dimethylcyclopropanecarboxylic acid.

3. A method as described in claim 1, wherein said 2,2-dimethylcyclopropanecarboxylic acid is a one containing the l-form in excess, and said optically active 2,2-dimethylcyclopropanecarboxylic acid is l-2,2-dimethylcyclopropanecarboxylic acid.

4. A method as described in claim 2, wherein the optical excess rate of said 2,2-dimethylcyclopropanecarboxylic acid is not less than 30%.

5. A method as described in claim 1, wherein said optically active diphenylethylamine is either of d- or l-α-phenyl-β-(p-tolyl)ethylamine, d- or l-α-(p-tolyl)-β-phenylethylamine or d- or l-α-phenyl-β-phenylethylamine.

6. A method as described in claim 1, wherein the amount of the optically active diphenylethylamine used is 0.3 to 1.2 times by mole based on 2,2-dimethylcyclopropanecarboxylic acid, a starting material.

7. A method as described in claim 3, wherein the optical excess rate of said 2,2-dimethylcyclopropanecarboxylic acid is not less than 30%.

* * * * *